(12) United States Patent
Tsuruta et al.

(10) Patent No.: US 8,932,060 B2
(45) Date of Patent: Jan. 13, 2015

(54) DENTAL TREATMENT METHOD

(71) Applicant: Kuraray Noritake Dental Inc., Kurashiki-shi (JP)

(72) Inventors: Takuo Tsuruta, Tainai (JP); Shumei Ishihara, Kurashiki (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 0 days.

(21) Appl. No.: 13/627,368

(22) Filed: Sep. 26, 2012

(65) Prior Publication Data

US 2013/0266915 A1 Oct. 10, 2013

(30) Foreign Application Priority Data

Sep. 30, 2011 (JP) ................. 2011-218741

(51) Int. Cl.
| | | |
|---|---|---|
| *A61C 5/00* | (2006.01) | |
| *A61K 6/00* | (2006.01) | |
| *A61K 6/02* | (2006.01) | |
| *A61K 6/027* | (2006.01) | |
| *A61K 6/033* | (2006.01) | |
| *A61K 6/06* | (2006.01) | |

(52) U.S. Cl.
CPC ................. *A61C 5/00* (2013.01); *A61K 6/0008* (2013.01); *A61K 6/0085* (2013.01); *A61K 6/0088* (2013.01); *A61K 6/0091* (2013.01); *A61K 6/024* (2013.01); *A61K 6/0273* (2013.01); *A61K 6/0276* (2013.01); *A61K 6/033* (2013.01); *A61K 6/0612* (2013.01)
USPC ......................................... 433/215; 433/226

(58) Field of Classification Search
USPC .................................. 433/215–226
See application file for complete search history.

(56) References Cited

U.S. PATENT DOCUMENTS

| | | | | |
|---|---|---|---|---|
| 4,150,485 | A | * | 4/1979 | Lee et al. ........................ 523/115 |
| 5,234,971 | A | | 8/1993 | Imai et al. |
| 5,554,669 | A | | 9/1996 | Nakabayashi et al. |
| 5,735,942 | A | * | 4/1998 | Litkowski et al. .............. 106/35 |
| 6,022,218 | A | * | 2/2000 | Alpert ............................ 433/215 |
| 2010/0048761 | A1 | * | 2/2010 | Ishino et al. ................... 523/116 |
| 2011/0165098 | A1 | * | 7/2011 | Jewett et al. ..................... 424/53 |
| 2012/0027829 | A1 | | 2/2012 | Hashimoto et al. |
| 2012/0135059 | A1 | | 5/2012 | Tsunekawa et al. |

FOREIGN PATENT DOCUMENTS

| | | | |
|---|---|---|---|
| JP | 6-57080 | | 3/1994 |
| JP | 3157153 | | 2/2001 |
| JP | 2007190226 | * | 8/2007 |
| JP | 2011-32250 | | 2/2011 |
| WO | WO 2012/046667 A1 | * | 4/2012 |

OTHER PUBLICATIONS

Machine Translation of JP2007190226 (2007).*

* cited by examiner

*Primary Examiner* — Edward Moran
(74) *Attorney, Agent, or Firm* — Oblon, Spivak, McClelland, Maier & Neustadt, L.L.P.

(57) ABSTRACT

Dentinal tubules sealing method using dentinal tubules sealant that is to be applied to a dentin surface to fill solid particles into dentinal tubules, wherein the dentinal tubules sealant comprises a water-based dispersing agent in which solid particles are dispersed and which has a solid/liquid ratio of from 0.3 to 2.6, and the method comprises applying the dentinal tubules sealant to a dentin surface to fill solid particles into dentinal tubules, and then removing a solid component adhering to the dentin surface by scrubbing using water. Thus, pains, hyperesthesia, and so on are allowed to be suppressed because dentinal tubules will be filled and sealed with solid particles and a curable composition is allowed to exhibit improved adhesive properties to a dentin surface because solid components adhering to the dentin surface can be removed by scrubbing using water.

6 Claims, No Drawings

DENTAL TREATMENT METHOD

TECHNICAL FIELD

The present invention relates to a dental treatment method using a dental treatment material comprising of dentinal tubules sealant and a curable composition in combination.

BACKGROUND ART

The suppression of a pain accompanying the exposure of dentin is a clinical problem. Examples of the cause of the dentin exposure include the retraction or wedge-shaped defect of the gum, abutment tooth formation, and cavity formation. In filling restoration or prosthesis mounting to an exposed dentin, adhesive curable compositions, such as a dental adhesive, have been used widely. In an adhering work using such a curable composition, a pain is caused easily because such operations as application of a composition containing an acidic monomer, and air blowing for evaporation of a solvent or removal of moisture are often carried out. Accordingly, inhibition of a pain in advance of an adhering work is required. Although the pathogenesis of a pain has not been elucidated completely, there has been known the hydrodynamic theory that an external stimulus causes movement of internal fluid of dentinal tubules to stimulate a pulp nerve. In order to control a pain, suppressing the movement of internal fluid of dentinal tubules by sealing dentinal tubules is known to be effective and various techniques have been proposed as a method for sealing dentinal tubules before an adhering work.

In Patent Document 1, there has been proposed a method for sealing dentinal tubules without impairing adhesive properties to a tooth structure by using an adhesive composition comprising an emulsion of polymer reactive with a constituent of the tooth structure, and it has been reported that it becomes possible to seal a dentine hypersensitivity surface.

In Patent Document 2, there has been proposed a dental treatment material that comprises two liquids containing a substance capable of forming a poorly soluble precipitate when being mixed and a photocurability composition that is applied to a precipitate formed by applying the two liquids one after another and then is cured together. According to this, it has been reported that a pulp stimulus can be intercepted and a filling material for dental use can be filled on it even if neither a commercially available dental cement nor dental lining material having been used as a base is filled.

In Patent Document 3, there has been proposed a buccal formulation comprising a liquid in which fluoroaluminosilicate glass fine particles are dispersed and an aqueous inorganic phosphoric acid solution. According to this, it has been reported that a large amount of fluoride is incorporated into teeth efficiently by a short-time treatment; impartation of high acid resistance, acceleration of remineralization, and prevention of secondary caries are enabled to be achieved; and a high effect of preventing dentine hypersensitivity can be acquired by the effect of closing dentinal tubules with fine particles generated during treatment, such as calcium fluoride, calcium phosphate, and silicate cement.

However, in the event that dentinal tubules are sealed by the methods disclosed in the above-cited Patent Documents 1 to 3 and then a dentin surface is bonded using a curable composition, good adhesion properties are not necessarily achieved and improvement has been desired.

PRIOR ART DOCUMENTS

Patent Documents

[Patent Document 1] JP 6-57080 A
[Patent Document 2] Japanese Patent No. 3157153
[Patent Document 3] JP 2011-32250 A

DISCLOSURE OF THE INVENTION

Problems to be Solved by the Invention

The present invention was devised in order to solve the above-described problems and an objective thereof is to provide a dental treatment method using dentinal tubules sealant that allows pains, hyperesthesia, and the like to be suppressed because dentinal tubules will be filled and sealed with solid particles and that allows a curable composition to exhibit improved adhesive properties to a dentin surface because solid components adhering to the dentin surface can be removed by scrubbing using water.

Means for Solving the Problems

The above-described problem is solved by providing a dental treatment method using dentinal tubules sealant that is to be applied to a dentin surface to fill solid particles into dentinal tubules, wherein the dentinal tubules sealant comprises a water-based dispersing agent in which solid particles are dispersed and which has a solid/liquid ratio of from 0.3 to 2.6, and the method comprises applying the dentinal tubules sealant to a dentin surface to fill solid particles into dentinal tubules, removing a solid component adhering to the dentin surface by scrubbing using water, and then applying a curable composition to the dentin surface from which the solid component has been removed, followed by curing the curable composition.

The above-described problem is solved also by providing a method for inhibiting dentinal hypersensitivity using a dentinal hypersensitivity inhibitor comprising dentinal tubules sealant that is to be applied to a dentin surface to fill solid particles into dentinal tubules, wherein the dentinal hypersensitivity inhibitor comprises a water-based dispersing agent in which solid particles are dispersed and which has a solid/liquid ratio of from 0.3 to 2.6, and the method comprises applying the dentinal hypersensitivity inhibitor to a dentin surface to fill solid particles into dentinal tubules, removing a solid component adhering to the dentin surface by scrubbing using water, and then applying a curable composition to the dentin surface from which the solid component has been removed, followed by curing the curable composition.

Effect of the Invention

By the present invention, it is possible to provide a dental treatment method using a dental treatment material that comprises dentinal tubules sealant and a curable resin composition in combination, that allows pains, hyperesthesia, and the like to be suppressed because dentinal tubules will be filled and sealed with solid particles, and that allows a curable composition to exhibit improved adhesive properties to a dentin surface because solid components adhering to the dentin surface can be removed by scrubbing using water. Moreover, it is also possible to provide a dental filling restoration method with respect to exposed dentin and a dental prosthesis restoration method using a prosthesis such as an inlay and a crown.

DETAILED DESCRIPTION OF THE INVENTION

The dental treatment method of the present invention is a dental treatment method using dentinal tubules sealant that is to be applied to a dentin surface to fill solid particles into dentinal tubules, the method being characterized in that the dentinal tubules sealant comprises a water-based dispersing agent in which solid particles are dispersed and which has a solid/liquid ratio of from 0.3 to 2.6, and that the method comprises applying the dentinal tubules sealant to a dentin surface to fill solid particles into dentinal tubules, then removing a solid component adhering to the dentin surface by scrubbing using water, and then applying a curable composition to the dentin surface from which the solid component has been removed, followed by curing the curable composition. By using dentinal tubules sealant comprising a water-based dispersing agent with a solid/liquid ratio of from 0.3 to 2.6 in which solid particles are dispersed as in the present invention, the dentinal tubules sealant exhibits good coating property and good capability of closing dentinal tubules. Moreover, since dentinal tubules sealant used in the present invention allows, after dentinal tubules are filled with solid particles, a solid component adhering to the dentin surface to be removed by scrubbing using water, the adhesion of a curable composition is not inhibited when the curable composition is applied to the dentin surface thereafter and then cured. Thus, pains, hyperesthesia, and so on are allowed to be suppressed because dentinal tubules will be filled and sealed with solid particles by the dentinal tubules sealant of the present invention before a curable composition is applied to a dentin surface, and a curable composition is allowed to exhibit improved adhesive properties to a dentin surface because solid components adhering to the dentin surface can be removed by scrubbing using water while solid particles filled in the dentinal tubules being held.

In the present invention, the solid particles to be used for the dentinal tubules sealant are not particularly restricted and may be inorganic particles, organic particles, or a mixture of inorganic particles and organic particles. From the viewpoint of biocompatibility or durability, the solid particles are preferably inorganic particles.

Examples of the inorganic particles to be used in the present invention include calcium compounds, such as calcium phosphate, calcium silicate, calcium carbonate, calcium hydrogencarbonate, calcium oxide, calcium hydroxide, calcium chloride, and calcium fluoride; silica, and silica or minerals containing silica as a base material, such as kaolin, clay, mica, and mica; ceramics and glass containing silica as a base material and also containing $Al_2O_3$, $B_2O_3$, $TiO_2$, $ZrO_2$, $BaO$, $La_2O_3$, $SrO$, $ZnO$, $CaO$, $P_2O_5$, $Li_2O$, $Na_2O$, etc. (lanthanum glass, barium glass, strontium glass, soda glass, lithium borosilicate glass, zinc glass, fluoroaluminosilicate glass, borosilicated glass, bioglass); and metal oxides, such as titania, alumina, zirconia, cerium oxide (ceria), hafnium oxide (hafnia), yttrium oxide (yttria), beryllium oxide (beryllia), niobium oxide (niobia), lanthanum oxide, bismuth oxide, tin oxide, zinc oxide, iron oxide, molybdenum oxide, nickel oxide, ytterbium oxide, samarium oxide, europium oxide, praseodymium oxide, magnesium oxide, and neodymium oxide. Among these, at least one kind of inorganic particles selected from the group consisting of calcium compounds, silica, or minerals containing silica as a base material are used preferably, and calcium compounds are used more preferably.

Among the above-mentioned calcium compounds, at least one kind of inorganic particles selected from the group consisting of calcium phosphate and calcium silicate are preferably used from a biocompatibility point of view, and calcium phosphate is used more preferably.

Examples of the above-mentioned calcium phosphate include tetracalcium phosphate $[Ca_4(PO_4)_2O]$ (this may be described as "TTCP"), anhydrous calcium hydrogen phosphate $[CaHPO_4]$ (this may be described as "DCPA"), anhydrous calcium dihydrogen phosphate $[Ca(H_2PO_4)_2]$, tricalcium phosphate $[Ca_3(PO_4)_2]$ (including amorphous calcium phosphate $[Ca_3(PO_4)_2.nH_2O]$, calcium pyrophosphate $[Ca_2P_2O_7]$, calcium dihydrogen pyrophosphate $[CaH_2P_2O_7]$, calcium hydrogen phosphate dihydrate $[CaHPO_4.2H_2O]$ (this may be described as "DCPD"), octacalcium phosphate pentahydrate $[Ca_8H_2(PO_4)_6.5H_2O]$, calcium pyrophosphate dihydrate $[Ca_2P_2O_7.2H_2O]$, calcium dihydrogen phosphate monohydrate $[Ca(H_2PO_4)_2.H_2O]$, and hydroxyapatite (this may be described as "HAp") $[Ca_{10}(PO_4)_6(OH)_2]$. Especially, since phosphate ions supplied to dentinal tubules react with calcium ions, so that HAp deposits and thus the dentinal tubules are closed with a dense sealant, at least one kind of calcium phosphate selected from the group consisting of tetracalcium phosphate $[Ca_4(PO_4)_2O]$, anhydrous calcium hydrogen phosphate $[CaHPO_4]$, calcium hydrogen phosphate dihydrate $[CaHPO_4.2H_2O]$, and tricalcium phosphate $[Ca_3(PO_4)_2]$ is preferably used, and at least one kind of calcium phosphate selected from the group consisting of tetracalcium phosphate $[Ca_4(PO_4)_2O]$, anhydrous calcium hydrogen phosphate $[CaHPO_4]$, and calcium hydrogen phosphate dihydrate $[CaHPO_4.2H_2O]$ is more preferably used.

Especially, the use of tetracalcium phosphate $[Ca_4(PO_4)_2O]$ and anhydrous calcium hydrogen phosphate $[CaHPO_4]$ in combination as the inorganic particles to be used for the dentinal tubules sealant is a preferred embodiment of the present invention. The blending ratio (TTCP/DCPA) in the case of using tetracalcium phosphate $[Ca_4(PO_4)_2O]$ and anhydrous calcium hydrogen phosphate $[CaHPO_4]$ together, which is not particularly limited, and is preferably from 1.5 to 5 and more preferably from 2 to 4.

Examples of the above-mentioned calcium silicate include calcium metasilicate $[CaSiO_3]$, calcium orthosilicate $[Ca_2SiO_4]$, and tricalcium silicate $[Ca_3SiO_5]$. Especially, tricalcium silicate $[Ca_3SiO_5]$ is preferably used from a biocompatibility point of view.

Examples of the organic particles to be used in the present invention include a melamine resin, an acrylic resin such as polymethyl methacrylate, polyimide, polystyrene, polyvinyl chloride, and polyester. Especially, from the viewpoint of strength at least one kind of organic particles selected from the group consisting of a melamine resin and polystyrene are preferably used.

The average particle diameter of the solid particles to be used for the dentinal tubules sealant, which is not particularly limited, is preferably 0.05 to 90 μm. When the average particle diameter is less than 0.05 μm, there is a possibility that dentinal tubules are sealed insufficiently, so that the effect of suppressing a pain, hyperesthesia, and so on will be reduced. The average particle diameter is more preferably 0.1 μm or more and even more preferably 0.5 μm or more. On the other hand, when the average particle diameter exceeds 90 μm, there is a possibility that dentinal tubules are sealed insufficiently, so that the effect of suppressing a pain, hyperesthesia, and so on will be reduced. The average particle diameter is more preferably 35 μm or less, even more preferably 30 μm or less.

A method for producing solid particles having such an average particle diameter is not particularly restricted. While commercial products may be used if available, it is often preferable to further grind a commercially available product.

In such a case, a grinding machine, such as a ball mill, a pestle and mortar machine and a jet mill, can be used.

The dentinal tubules sealant to be used by the present invention comprises a water-based dispersing agent in which solid particles are dispersed and which has a solid/liquid ratio of from 0.3 to 2.6. When the solid/liquid ratio of the dentinal tubules sealant is less than 0.3, it becomes difficult to apply the dentinal tubules sealant to a dentin surface due to the excessively high flowability of the water-based dispersing agent, so that it may become impossible to seal dentinal tubules. The solid/liquid ratio is preferably 0.4 or more, more preferably 0.6 or more, and even more preferably 0.8 or more. On the other hand, when the solid/liquid ratio of the dentinal tubules sealant exceeds 2.6, it becomes difficult to apply the dentinal tubules sealant to a dentin surface due to the excessively low flowability of the water-based dispersing agent, so that it may become impossible to seal dentinal tubules. The solid/liquid ratio is preferably 2.5 or less, more preferably 2.2 or less, and even more preferably 2.0 or less.

The dentinal tubules sealant to be used in the present invention may comprise components other than the solid particles described above as long as the effect of the present invention is not impaired. For example, an alkali metal salt of phosphoric acid, a fluorine compound, a thickener, etc. may be incorporated.

The alkali metal salt of phosphoric acid is not particularly restricted, and examples thereof include disodium hydrogen phosphate, dipotassium hydrogen phosphate, lithium dihydrogen phosphate, sodium dihydrogen phosphate, potassium dihydrogen phosphate, trisodium phosphate, tripotassium phosphate, and so on, among which one salt or two or more salts are used. Particularly, from the viewpoint of safety or easiness of obtaining a raw material with high purity, it is preferred that the alkali metal salt of phosphoric acid be disodium hydrogen phosphate and/or sodium dihydrogen phosphate. Moreover, from the viewpoint of safety, it is preferred that the alkali metal ion in the alkali metal salt of phosphoric acid be a sodium ion.

The fluorine compound is not particularly restricted, and examples thereof include sodium fluoride, potassium fluoride, ammonium fluoride, lithium fluoride, cesium fluoride, magnesium fluoride, calcium fluoride, strontium fluoride, barium fluoride, copper fluoride, zirconium fluoride, aluminum fluoride, stannous fluoride, sodium monofluorophosphate, potassium monofluorophosphorate, hydrofluoric acid, titanium sodium fluoride, titanium potassium fluoride, hexylamine hydrofluoride, laurylamine hydrofluoride, glycine hydrofluoride, alanine hydrofluoride, fluorosilanes, and diamine silver fluoride. Among these, sodium fluoride, sodium monofluorophosphate, and stannous fluoride are suitably used from the viewpoint of safety.

The thickener is not particularly restricted and may be, for example, one or two or more species selected from carboxymethylcellulose, sodium carboxymethylcellulose, hydroxypropylcellulose, hydroxypropylmethylcellulose, polyvinyl alcohol, polyethylene glycol, polyacrylic acid, polystyrene sulfonic acid, polystyrene sulfonic acid salts, polyglutamic acid, polyglutamic acid salts, polyaspartic acid, polyaspartic acid salts, poly-L-lysine, poly-L-lysine salts, starch other than cellulose, alginic acid, alginic acid salts, carrageenan, guar gum, xanthan gum, cellulose gum, hyaluronic acid, hyaluronic acid salts, polysaccharides such as pectin, pectin salts, chitin and chitosan, acidic polysaccharide esters such as propylene glycol alginate, and polymers such as proteins, e.g. collagen, gelatin and their derivatives. From aspects of solubility in water and viscosity, preferred is at least one species chosen from sodium carboxymethylcellulose, hydroxypropylcellulose, hydroxypropylmethylcellulose, alginic acid, alginic acid salts, chitosan, polyglutamic acid and polyglutamic acid salts.

According to need, polyhydric alcohols, such as glycerol, ethylene glycol, propylene glycol, and diglycerol; sugar alcohols, such as xylitol, sorbitol, and erythritol; polyethers, such as polyethylene glycol and polypropylene glycol; artificial sweeteners, such as aspartame, acesulfame potassium, liquorice extract, saccharin, and saccharin sodium; and so on may also be added. Moreover, all pharmacologically acceptable drugs can be blended. For example, antibacterial agents typified by cetyl pyridinium chloride etc., disinfectants, anticancer drugs, antibiotics, blood circulation improvers, such as Actosin and PEG1, growth factors, such as bFGF, PDGF, and BMP, cells which promote hard tissue formation, such as osteoblasts, odontoblasts, and anaplastic bone marrow derived stem cells, embryonic stem (ES) cells, induced pluripotent stem (iPS) cells produced by dedifferentiating differentiated cells such as fibroblasts by gene introduction, and cells produced by differentiating the foregoing, can be blended.

While the dentinal tubules sealant to be used in the present invention comprises a water-based dispersing agent in which the solid particles described above are dispersed, a liquid containing water as a main component or a water-based paste is used suitably as the liquid agent to disperse the solid particles in the water-based dispersing agent. Here, the liquid containing water as a main component may be either pure water or a liquid containing water as a main component and also containing other components. The water-based paste containing water as a main component indicates a paste-like liquid containing water as a main component and also containing other components. The other components are not particularly restricted, and examples thereof include polyhydric alcohols such as glycerol, ethylene glycol, propylene glycol, and diglycerol; sugar alcohols such as xylitol, sorbitol, and erythritol; polyethers such as polyethylene glycol and polypropylene glycol.

The dental treatment method of the present invention is characterized by applying the dentinal tubules sealant to a dentin surface to fill solid particles into dentinal tubules, removing a solid component adhering to the dentin surface by scrubbing using water, and then applying a curable composition to the dentin surface from which the solid component has been removed, followed by curing the curable composition. Specifically, since the dentinal tubules sealant to be used in the present invention allows, after it is applied to a dentin surface and thereby dentinal tubules are filled with solid particles, a solid component adhering to the dentin surface to be removed by scrubbing using water, the adhesion of a curable composition is not inhibited when the curable composition is applied to the dentin surface thereafter and then cured. As described above, pains, hyperesthesia, and so on are allowed to be suppressed because dentinal tubules will be filled and sealed with solid particles in advance by the dentinal tubules sealant of the present invention before a curable composition is applied to a dentin surface, and a curable composition is allowed to exhibit improved adhesive properties to a dentin surface because solid components adhering to the dentin surface can be removed by scrubbing using water.

The lowering of adhesive properties to a tooth structure will cause fall off of a filling restoration or a prosthesis or secondary caries due to invasion of bacteria into an exfoliated peripheral area. Accordingly, in the event that dentinal tubules are sealed before filling restoration or prosthesis mounting to an exposed dentin, it is required that adhesive properties should not be lowered by the use of dentinal tubules sealant. As shown by the results of adhesion strength in Comparative Examples 8 to 10 described below, the study performed by the present inventors has shown that when treating with the adhesive composition disclosed in Patent Document 1, a thin film is formed on the surface of a tooth structure and thereby dentinal tubules are sealed, but adhesion strength lowers because of insufficient adhesive properties between the thin film and the surface of the tooth structure. Moreover, it has been shown that when treating with the dental treatment disclosed in Patent Document 2, a thin film containing a deposit is formed on a surface of a tooth structure and thereby dentinal tubules are sealed, but adhesion strength lowers due to insufficient strength of the deposit. Furthermore, it has been shown that when treating with the buccal formulation disclosed in Patent Document 3, a thin film of fine particles is formed on a surface of a tooth structure and dentinal tubules are sealed, but adhesion strength lowers due to insufficient strength of the thin film.

On the other hand, the present inventors have confirmed that in the event that dentinal tubules sealant to be used in the present was applied to a dentin surface, then a solid component adhering to the dentin surface was removed by scrubbing using water, and then a curable composition was applied to the dentin surface, there was achieved adhesion strength comparable to that attained when the curable composition was applied to a dentin surface without using the dentinal tubules sealant. Accordingly, it is very worthy to adopt the dentinal tubules sealing method of the present invention by which pains, hyperesthesia, and so on are allowed to be suppressed because dentinal tubules will be filled and sealed with solid particles and a curable composition is allowed to exhibit improved adhesive properties to a dentin surface because solid components adhering to the dentin surface can be removed by scrubbing using water.

In order to fill solid particles into dentinal tubules by applying dentinal tubules sealant to be used in the present invention to a dentin surface, it is preferable to apply the dentinal tubules sealant to the dentin surface and then perform an operation to rub the applied dentinal tubules sealant into dentinal tubules with a microbrush, a cotton swab, a rubber cup, or the like. The operation of rubbing may be only rubbing the dentin surface with a microbrush or the like for about 30 seconds, whereby solid particles can be filled into dentinal tubules. The present inventors have confirmed that it is impossible to fill solid particles into dentinal tubules having a diameter of about 2 μm to seal the dentinal tubules by only applying dentinal tubules sealant to be used in the present invention to a dentin surface and leaving it at rest for several minutes. Accordingly, dentinal tubules sealant to be used for sealing dentinal tubules by rubbing it into dentinal tubules is a preferred embodiment of the present invention.

In the present invention, the method for removing a solid component adhering to a dentin surface by scrubbing using water is not particularly restricted, and the solid component adhering to the dentin surface can be removed well by scrubbing by using an applicator impregnated with water, such as a cotton ball, a microbrush, a sponge, a cotton swab, and a small brush. On the other hand, as shown by the comparison of the examples and the comparative examples described later, the present inventors has confirmed that when cleaning a dentin surface by merely wiping or when cleaning a dentin surface with running water only, the adhesive properties of a curable composition are impaired. Accordingly, it is significant to use dentinal tubules sealant that allows a solid component adhering to a dentin surface to be removed by scrubbing using water.

The curable composition to be used in the present invention is a composition that is applied to a dentin surface from which a solid component has been removed and then is cured. The curable composition is preferably a composition that contains a monomer component and can cure through polymerization of the monomer component. The curable composition to be used in the present invention is used suitably as a bonding material, an adhesive composite resin, an adhesive cement, and so on and is used more suitably as a bonding material and an adhesive cement.

Here, an adhesive system in the case of using a curable composition to a dentin surface is one including an decalcifying step of dissolving a dentin surface with an acidic component, a permeation step of allowing a monomer component to permeate into a collagen layer of the dentin, and a curing step of allowing the monomer component thus penetrated to solidify to form a hybrid layer (hereinafter sometimes referred to as a "resin-impregnated layer") with collagen. Basically, a product used for the penetration step is a primer, and a product used for the curing step is a bonding material.

As the above-mentioned adhesive system, a total etching system may be adopted in which a decalcifying step of dissolving a dentin surface with an acidic component such as phosphoric acid (this step may hereinafter be described as "acid etching") is performed and further a curing step is performed using a bonding material after performing a water washing-drying step; a two-component, two-step adhesive system may be adopted in which a self etching primer that allows a decalcifying step and a penetration step to be performed in one stage, and a bonding material are used; and a one-component, one-step adhesive system may be adopted in which a bonding material which allows a decalcifying step, a penetration step, and a curing step to be performed together in one stage.

The curable composition to be used in the present invention preferably contains a polymerizable monomer (a) having an acidic group, a hydrophilic polymerizable monomer (b), a crosslinkable polymerizable monomer (c), a solvent (d), a polymerization initiator (e), a polymerization accelerator (f), a filler (g), etc. depending on the implementation. A detailed description is made below.

[Polymerizable Monomer (a) Having an Acidic Group]

Examples of the polymerizable monomer (a) having an acidic group include polymerizable monomers having at least one acidic group such as a phosphoric acid group, a pyrophosphoric acid group, a thiophosphoric acid group, and a phosphonic acid group and having at least one polymerizable group such as an acryloyl group, a methacryloyl group, a vinyl group, and a styrene group. By having a polymerizable group, it becomes possible to undergo radical polymerization and also becomes possible to undergo copolymerization with other monomers. From the viewpoint of polymerizability, the polymerizable group is preferably a (meth)acrylic group or a (meth)acrylamide group. Moreover, since the polymerizable monomer (a) having an acidic group has an acidic group such as a phosphoric acid group, a pyrophosphoric acid group, a thiophosphoric acid group, and a phosphonic acid group as well as has the above-described polymerizable group. Therefore, it has advantages that, for example, pretreatments such as an acid etching treatment and a primer treatment are not necessary since the polymerizable monomer (a) itself, that has an acidic group, has an acid-etching effect and a primer treatment effect.

Examples of the polymerizable monomer (a) having a phosphoric acid group include 2-(meth)acryloyloxyethyl dihydrogenphosphate, 3-(meth)acryloyloxypropyl dihydrogenphosphate, 4-(meth)acryloyloxybutyl dihydrogenphosphate, 5-(meth)acryloyloxypentyl dihydrogenphosphate, 6-(meth)acryloyloxyhexyl dihydrogenphosphate, 7-(meth)acryloyloxyheptyl dihydrogenphosphate, 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyicosyl dihydrogenphosphate, bis[2-(meth)acryloyloxyethyl]hydrogenphosphate, bis[4-(meth)acryloyloxybutyl]hydrogenphosphate, bis[6-(meth)acryloyloxyhexyl]hydrogenphosphate, bis[8-(meth)acryloyloxyoctyl]hydrogenphosphate, bis[9-(meth)acryloyloxynonyl]hydrogenphosphate, bis[10-(meth)acryloyloxydecyl]hydrogenphosphate, 1,3-di(meth)acryloyloxypropyl dihydrogenphosphate, 2-(meth)acryloyloxyethylphenyl hydrogenphosphate, 2-(meth)acryloyloxyethyl-2-bromoethyl hydrogenphosphate, bis[2-(meth)acryloyloxy-(1-hydroxymethyl)ethyl] hydrogenphosphate, and their acid chlorides, alkali metal salts, ammonium salts, etc.

Examples of the polymerizable monomer (a) having a pyrophosphoric acid group include bis[2-(meth)acryloyloxyethyl]pyrophosphorate, bis[4-(meth)acryloyloxybutyl]pyrophosphorate, bis[6-(meth)acryloyloxyhexyl]pyrophosphorate, bis[8-(meth)acryloyloxyoctyl]pyrophosphorate, bis[10-(meth)acryloyloxydecyl]pyrophosphorate, and their acid chlorides, alkali metal salts, ammonium salts, etc.

Examples of the polymerizable monomer (a) having a thiophosphoric acid group include 2-(meth)acryloyloxyethyl dihydrogenthiophosphate, 3-(meth)acryloyloxypropyl dihydrogenthiophosphate, 4-(meth)acryloyloxybutyl dihydrogenthiophosphate, 5-(meth)acryloyloxypentyl dihydrogenthiophosphate, 6-(meth)acryloyloxyhexyl dihydrogenthiophosphate, 7-(meth)acryloyloxyheptyl dihydrogenthiophosphate, 8-(meth)acryloyloxyoctyl dihydrogenthiophosphate, 9-(meth)acryloyloxynonyl dihydrogenthiophosphate, 10-(meth)acryloyloxydecyl dihydrogenthiophosphate, 11-(meth)acryloyloxyundecyl dihydrogenthiophosphate, 12-(meth)acryloyloxydodecyl dihydrogenthiophosphate, 16-(meth)acryloyloxyhexadecyl dihydrogenthiophosphate, 20-(meth)acryloyloxyicosyl dihydrogenthiophosphate, and their acid chlorides, alkali metal salts, ammonium salts, etc.

Examples of the polymerizable monomer (a) having a phosphonic acid group include 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and their acid chlorides, alkali metal salts, ammonium salts, etc.

Among the above-mentioned polymerizable monomers (a) having an acidic group, from the viewpoint of adhesion strength, a polymerizable monomer (a) having an acidic group preferably has a phosphoric acid group or a phosphonic acid group and more preferably has a phosphoric acid group.

The amount of the polymerizable monomer (a) having an acidic group to be added may be determined appropriately depending on the implementation, and it is preferred that the polymerizable monomer (a) be contained in 1 to 90 parts by weight, more preferably in 2 to 80 parts by weight relative to 100 parts by weight of the whole amount of the polymerizable monomer components. When the amount of the polymerizable monomer (a) having an acidic group to be added is less than 1 part by weight, a sufficient decalcifying effect is not acquired, so that adhesion strength may lower. On the other hand, when the amount of the polymerizable monomer (a) having an acidic group to be added exceeds 90 parts by weight, sufficient curability is not acquired, so that adhesion strength may lower.

[Hydrophilic Polymerizable Monomer (b)]

Examples of the hydrophilic polymerizable monomer (b) include polymerizable monomers that are other than the above-described polymerizable monomers (a) having an acidic group and that have one or more hydroxyl groups and at least one polymerizable group, and (meth)acrylamide compounds that contain no hydroxyl groups and exhibit a solubility in water at 25° C. of 10% by weight or more. Polymerizable monomers having one or more hydroxyl groups and at least one polymerizable group are sufficiently hydrophilic because they have one or more hydroxyl groups, and they are better in permeability to a collagen layer of dentin and exhibit enhanced adhesion strength because they are polymerizable monomers having at least one polymerizable group. Regarding the hydrophilic polymerizable monomer (b), the polymerizable group is preferably a (meth)acryl group or a (meth)acrylamide group from the viewpoint of radical polymerizability.

Examples of the hydrophilic polymerizable monomer (b) include 2-hydroxyethyl(meth)acrylate, 3-hydroxypropyl(meth)acrylate, 4-hydroxybutyl(meth)acrylate, 6-hydroxyhexyl(meth)acrylate, 10-hydroxydecyl(meth)acrylate, propyleneglycol mono(meth)acrylate, glycerol mono(meth)acrylate, erythritol mono(meth)acrylate, N-methylol(meth)acrylamide, N-hydroxyethyl(meth)acrylamide, N,N-(dihydroxyethyl)(meth)acrylamide, diacetone(meth)acrylamide, and 4-(meth)acryloylmorpholine. From the viewpoint of improvement in permeability into a collagen layer of dentin, preferred are 2-hydroxyethyl(meth)acrylate, 3-hydroxypropyl(meth)acrylate, glycerol mono(meth)acrylate, erythritol mono(meth)acrylate, and 4-(meth)acryloylmorpholine, and particularly preferred is 2-hydroxyethyl methacrylate.

The amount of the hydrophilic polymerizable monomer (b) to be added may be determined appropriately depending on the implementation, and it is preferred that the hydrophilic polymerizable monomer (b) be contained in 1 to 90 parts by weight, more preferably in 2 to 80 parts by weight relative to 100 parts by weight of the whole amount of the polymerizable monomer components. When the amount of the hydrophilic polymerizable monomer (b) to be added is less than 1 part by weight, a sufficient effect to penetrate into a collagen layer of dentin is not acquired, so that adhesion strength may lower. On the other hand, when the amount of the hydrophilic polymerizable monomer (b) to be added exceeds 90 parts by weight, sufficient curability is not acquired, so that adhesion strength may lower.

[Crosslinkable Polymerizable Monomer (c)]

The crosslinkable polymerizable monomer (c) may be used alone or two or more kinds thereof may be used in combination. And examples of the crosslinkable polymerizable monomer (c) include an aromatic compound-based bifunctional polymerizable monomer, an aliphatic compound-based bifunctional polymerizable monomer, and trifunctional or higher polymerizable monomers.

Examples of the aromatic compound-based bifunctional polymerizable monomer include 2,2-bis((meth)acryloyloxyphenyl)propane, 2,2-bis[4-(3-(meth)acryloyloxy)-2-hydroxypropoxyphenyl]propane (commonly known as "Bis-GMA"), 2,2-bis(4-(meth)acryloyloxyphenyl)propane, 2,2-bis(4-(meth)acryloyloxypolyethoxyphenyl)propane, 2,2-bis(4-(meth)acryloyloxydiethoxyphenyl)propane, 2,2-bis(4-

(meth)acryloyloxytetraethoxyphenyl)propane, 2,2-bis(4-(meta)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxydiethoxyphenyl)propane, 2-(4-(meth)acryloyloxydiethoxyphenyl)-2-(4-(meth)acryloyloxyditriethoxyphenyl)propane, 2-(4-(meta)acryloyloxydipropoxyphenyl)-2-(4-(meta)acryloyloxy triethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl) pyromellitate.

Examples of the aliphatic compound-based bifunctional polymerizable monomer include ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy) ethane, and 2,2,4-trimethylhexamethylenebis(2-carbamoyloxyethyl)dimethacrylate (commonly known as "UDMA").

Examples of the trifunctional or higher polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

The amount of the crosslinkable polymerizable monomer (c) to be added may be determined appropriately depending on the implementation, and it is more preferred that the polymerizable monomer (c) be contained in 1 to 90 parts by weight, more preferably in 2 to 80 parts by weight relative to 100 parts by weight of the amount of the polymerizable monomer components. When the amount of the crosslinkable polymerizable monomer (c) to be added is less than 1 part by weight, adhesion strength produced by the crosslinkable polymerizable monomer (c) may lower. On the other hand, when the amount of the crosslinkable polymerizable monomer (c) to be added exceeds 90 parts by weight, the permeability of the composition to the collagen layer of dentin becomes insufficient, so that satisfactory adhesion strength may no longer be obtained.

[Solvent (d)]

Examples of the solvent (d) include water, organic solvents, and mixed solvents thereof. Examples of the organic solvents include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Particularly, when both safety to biological bodies and easy removal based on volatility are taken into consideration, the solvent (d) is preferably a water-soluble solvent, i.e., at least one member selected from the group consisting of water and water-soluble organic solvents. Specifically, at least one selected from the group consisting of water, ethanol, 2-propanol, 2-methyl-2-propanol, and acetone is used preferably.

The content of the solvent (d) is not particularly limited, and no incorporation of the organic solvent is needed in some embodiments. In an embodiment using the above-mentioned organic solvent, it is preferred that the organic solvent be contained in 1 to 2000 parts by weight relative to 100 parts by weight of the whole amount of polymerizable monomer components. The preferable amount of the solvent (d) to be added varies considerably depending on the embodiment in which it is used. Therefore, preferable amounts of solvents to be added according to respective embodiments are indicated together with description of specific embodiments of the curable composition described later.

[Polymerization Initiator (e)]

The polymerization initiator (e) can be selected from polymerization initiators commonly used in the industrial field. Among them, polymerization initiators used for dental applications are used preferably. Particularly, photopolymerization initiators and chemical polymerization initiators can be used independently or two or more of them can be used in suitable combination.

Examples of the photopolymerization initiator include (bis)acylphosphine oxides, water-soluble acyiphosphine oxides, thioxanthones or the quaternary ammonium salts of thioxanthones, ketals, α-diketones, coumarins, anthraquinones, benzoin alkyl ether compounds, and α-amino ketone compounds.

While 2,4,6-trimethylbenzoyldiphenylphosphine oxide, 2,4,6-trimethylbenzoylmethoxyphenylphosphine oxide, bis (2,4,6-trimethylbenzoyl)phenylphosphineoxide, a sodium salt of 2,4,6-trimethylbenzoylphenylphosphineoxide, and so on can be used suitably as the (bis)acylphosphine oxides and the water-soluble acylphosphine oxides to be used as the photopolymerization initiator, the (bis)acylphosphine oxides and the water-soluble acylphosphine oxides disclosed in WO 2008/087977 A can also be used.

While 2-chlorothioxanthen-9-one, 2-hydroxy-3-(3,4-dimethyl-9H-thioxanthen-2-yloxy)-N,N,N-trimethyl-1-propaneaminium chloride, and so on can be used suitably as the thioxanthone or quaternary ammonium salt of thioxanthone to be used as the photopolymerization initiator, the thioxanthones or quaternary ammonium salts of thioxanthones disclosed in WO 2008/087977 A can also be used.

Examples of ketals used as the photopolymerization initiator include benzyl dimethyl ketal and benzyl diethyl ketal.

Examples of the α-diketones used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

While 3,3'-carbonylbis(7-diethylamino)coumarin, 3,3'-carbonylbis(7-dibutylamino)coumarin, and so on can be used as a coumarin compound to be used as the photopolymerization initiator, the coumarin compounds disclosed in WO 2008/087977 A can also be used.

Examples of the anthraquinones used as the aforementioned photopolymerization initiator include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers used as the aforementioned photopolymerization initiator include benzoin methyl ether, benzoin ethyl ether, benzoin isopropyl ether, and benzoin isobutyl ether.

Examples of the α-aminoketones used as the aforementioned photopolymerization initiator include 2-methyl-1-[4-(methylthio)phenyl]-2-morpholinopropan-1-one.

Preferably, among these photopolymerization initiators, at least one selected from the group consisting of (bis)acylphosphine oxides, salts thereof, α-diketones, and coumarin compounds is used. This makes it possible to obtain a curable composition that has excellent photocurability in visible and near-ultraviolet ranges and sufficiently high photocurability regardless of which light source among a halogen lamp, light-emitting diode (LED), and xenon lamp is used.

Among the polymerization initiators (e), a chemical polymerization initiator that is used preferably is organic peroxide. The organic peroxide used as the chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate.

Examples of hydroperoxide used as the chemical polymerization initiator include 2,5-dimethylhexane-2,5-dihydroperoxide, diisopropylbenzene hydroperoxide, cumene hydroperoxide, t-butylhydroperoxide, and 1,1,3,3-tetramethylbutyl hydroperoxide.

Examples of diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

The dialkyl peroxides to be used as the above-mentioned chemical polymerization initiator include di-tert-butyl peroxide, dicumyl peroxide, tert-butyl cumyl peroxide, 2,5-dimethyl-2,5-di-(tert-butylperoxy)hexane, 1,3-bis(tert-butylperoxyisopropyl)benzene, and 2,5-dimethyl-2,5-di(tert-butyl peroxy)-3-hexyne.

Examples of the ketone peroxide, peroxyketal, peroxyester, and peroxydicarbonate to be used as the above-mentioned chemical polymerization initiator include those disclosed in WO 2008/087977 A.

Among these organic peroxides, diacyl peroxide is used preferably from the viewpoint of a comprehensive balance of safety, storage stability, and radical production ability, and among these, benzoyl peroxide is used particularly preferably.

The amount of polymerization initiator (e) to be added may be determined appropriately depending on the implementation, and from the viewpoint of, for example, curability of the resultant composition, it is preferable that 0.001 to 30 parts by weight of polymerization initiator (e) be contained with respect to 100 parts by weight of the whole amount of polymerizable monomer components. When the amount of polymerization initiator (e) to be added is less than 0.001 parts by weight, polymerization may not proceed sufficiently and thereby adhesion strength may be reduced. Therefore, the amount is more preferably at least 0.05 parts by weight. On the other hand, when the amount of polymerization initiator (e) to be added exceeds 30 parts by weight, in the case where the polymerization initiator itself has low polymerization performance, sufficiently high adhesion strength may not be obtained and further precipitation from the composition may occur. Therefore, the amount is more preferably 20 parts by weight or less.

[Polymerization Accelerator (f)]

Examples of the polymerization accelerator (f) include amines, sulfinic acids and salts thereof, borate compounds, barbituric acid derivatives, triazine compounds, copper compounds, tin compounds, vanadium compounds, halogen compounds, aldehydes, thiol compounds, sulfite, bisulfite, and thiourea compounds. Specific examples thereof include those disclosed in WO 2008/087977 A.

The amount of polymerization accelerator (f) to be added may be determined appropriately depending on the implementation, and from the viewpoint of, for example, curability of the resultant composition, it is preferable that 0.001 to 20 parts by weight of polymerization accelerator (f) be contained with respect to 100 parts by weight of the whole amount of polymerizable monomer components. When the amount of polymerization accelerator (f) to be added is less than 0.001 parts by weight, polymerization may not proceed sufficiently and adhesion strength may be reduced. Therefore, the amount is more preferably at least 0.05 parts by weight. On the other hand, when the amount of polymerization accelerator (f) to be added exceeds 20 parts by weight, in the case where the polymerization initiator itself has low polymerization performance, sufficiently high adhesion strength may not be obtained and further precipitation from the composition may occur. Therefore, the amount is more preferably 10 parts by weight or less.

[Filler (g)]

Generally, the filler (g) is divided roughly into organic fillers, inorganic fillers, and organic-inorganic composite fillers. Examples of materials for the organic fillers includes polymethyl methacrylate, polyethyl methacrylate, methyl methacrylate-ethyl methacrylate copolymer, crosslinked type polymethyl methacrylate, crosslinked type polyethyl methacrylate, polyamide, polyvinyl chloride, polystyrene, polychloroprene rubber, nitrile rubber, ethylene-vinyl acetate copolymer, styrene-butadiene copolymer, acrylonitrile-styrene copolymer, and acrylonitrile-styrene-butadiene copolymer. These may be used singly or in the form of a mixture of two or more of them. The shapes of the organic fillers are not particularly limited, and particle sizes of the fillers to be used can be selected appropriately. From the viewpoints of, for example, handling ability and mechanical strength of the resultant composition, the mean particle size of the organic fillers is preferably 0.001 to 50 μm and more preferably 0.001 to 10 μm.

Examples of the inorganic fillers include quartz, silica, alumina, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may also be used singly or in the form of a mixture of two or more of them. The shapes of the inorganic fillers are not particularly limited and particle sizes of the fillers to be used can be selected appropriately. From the viewpoints of, for example, handling ability and mechanical strength of the resultant composition, the mean particle size of the inorganic fillers is preferably 0.001 to 50 μm and more preferably 0.001 to 10 μm.

Examples of the shapes of the inorganic fillers include amorphous fillers and spherical fillers. From the viewpoint of improving the mechanical strength of a composition, it is preferable that spherical fillers be used as the inorganic fillers. Furthermore, in the case of using the spherical fillers, when a curable composition is used as a dental composite resin, there also is an advantage that a composite resin with excellent surface smoothness is obtained. In this case, the spherical fillers are fillers in which when a photograph thereof is taken with a scanning electron microscope (hereinafter abbreviated as SEM), particles observed within a unit field of view are rounded and the mean uniformity obtained by dividing the particle size in the direction orthogonal to the maximum diameter by the maximum diameter is at least 0.6. The mean particle size of the spherical fillers is preferably 0.1 to 5 μm. When the mean particle size is less than 0.1 μm, the filling rate of the spherical fillers in the composition decreases and thereby the mechanical strength may be reduced. On the other hand, when the mean particle size exceeds 5 µm, the surface areas of the spherical fillers are reduced and a cured body with high mechanical strength may not be obtained.

The inorganic fillers may be used after the surfaces thereof are treated beforehand with a known surface-treating agent such as a silane coupling agent in order to adjust fluidity of the composition as required. Examples of such a surface-treating agent include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

An organic-inorganic composite filler is a material obtainable by adding a monomer compound to the aforementioned inorganic filler beforehand to form a paste-like material, polymerizing it, followed by pulverization. The organic-inorganic composite filler that can be used is, for example, a TMPT filler (obtained by mixing trimethylolpropane methacrylate with a silica filler, polymerizing it, and then crushing it). The shape of the organic-inorganic composite filler is not particularly limited, and the particle size of the filler to be used can be selected appropriately. From the viewpoints of, for example, handling ability and mechanical strength of the resultant composition, the mean particle size of the organic-inorganic composite filler is preferably 0.001 to 50 µm and more preferably 0.001 to 10 µm.

Regarding the amount of the filler (g) to be added, it is preferable that the filler (g) be contained in 1 to 2000 parts by weight with respect to 100 parts by weight of the whole amount of the polymerizable monomer components. The preferable amount of the filler (g) to be added varies considerably depending on the embodiment to be employed. Accordingly, preferable loadings of the filler (g) according to the respective embodiments are indicated together with description of specific embodiments of the curable composition described later.

In addition, for example, a pH adjuster, a polymerization inhibitor, an ultraviolet absorbent, a thickening agent, a colorant, an antibacterial agent, and a flavor may be incorporated into the curable composition as long as the effect of the present invention is not impaired.

In the following, preferable embodiments of the curable composition, a bonding material used for a total etching system (this may hereinafter be described as a "total etching type bond"), a bonding material to be used for a two-component, two-step adhesive system (this may hereinafter be described as a "two-component self etching type bond"), a bonding material to be used for a one-component, one-step adhesive system (this may hereinafter be described as a "one-component self etching type bond"), an adhesive composite resin, and an adhesive cement, will be described in detail.

[Total Etching Type Bond]

Preferably, the total etching type bond is a composition comprising a polymerizable monomer (a) having an acidic group, a hydrophilic polymerizable monomer (b), a crosslinkable polymerizable monomer (c), a solvent (d), a polymerization initiator (e), and a polymerization accelerator (f). To subject a dentin surface from which a solid component has been removed to an acid etching treatment using an acidic component such as phosphoric acid, then perform a water washing-drying step, and then apply a total etching type bond is one preferred embodiment of the present invention.

Regarding the amounts of the respective components to be added in the total etching type bond, it is preferred that the polymerizable monomer (a) having an acidic group be contained in 0 to 40 parts by weight, the polymerizable hydrophilic monomers (b) be contained in 0 to 80 parts by weight and the polymerizable crosslinkable monomers (c) be contained in 1 to 90 parts by weight relative to 100 parts by weight of the whole amount of the polymerizable monomer components, and it is more preferred that the polymerizable monomer (a) having an acidic group be contained in 3 to 30 parts by weight, the polymerizable hydrophilic monomers (b) be contained in 10 to 60 parts by weight and the polymerizable crosslinkable monomers (c) be contained in 10 to 60 parts by weight. Moreover, it is preferred that the solvent (d) be contained in 1 to 1000 parts by weight, the polymerization initiator (e) be contained in 0.001 to 30 parts by weight, and the polymerization accelerator (f) be contained in 0.001 to 20 parts by weight relative to 100 parts by weight of the whole amount of the polymerizable monomer components, and it is more preferred that the solvent (d) be contained in 5 to 500 parts by weight, the polymerization initiator (e) be contained in 0.05 to 20 parts by weight, and the polymerization accelerator (f) be contained in 0.05 to 10 parts by weight.

[Two-Component Self Etching Type Bond]

In the present invention, the two-component self etching type bond is a material to be used together with a self etching primer that allows a decalcifying step and a penetration step to be performed in one stage. Preferably, the self etching primer is a composition comprising a polymerizable monomer (a) having an acidic group, a hydrophilic polymerizable monomer (b), a crosslinkable polymerizable monomer (c), a solvent (d), a polymerization initiator (e), and a polymerization accelerator (f).

Regarding the amounts of the respective components to be added in the self etching primer, it is preferred that the polymerizable monomer (a) having an acidic group be contained in 1 to 90 parts by weight, the polymerizable hydrophilic monomers (b) be contained in 1 to 90 parts by weight and the polymerizable crosslinkable monomers (c) be contained in 0 to 60 parts by weight relative to 100 parts by weight of the whole amount of the polymerizable monomer components, and it is more preferred that the polymerizable monomer (a) having an acidic group be contained in 2 to 80 parts by weight, the polymerizable hydrophilic monomers (b) be contained in 2 to 80 parts by weight and the polymerizable crosslinkable monomers (c) be contained in 0 to 50 parts by weight. Moreover, it is preferred that the solvent (d) be contained in 1 to 3500 parts by weight, the polymerization initiator (e) be contained in 0.001 to 30 parts by weight, and the polymerization accelerator (f) be contained in 0.001 to 30 parts by weight relative to 100 parts by weight of the whole amount of the polymerizable monomer components, and it is more preferred that the solvent (d) be contained in 5 to 1000 parts by weight, the polymerization initiator (e) be contained in 0.05 to 20 parts by weight, and the polymerization accelerator (f) be contained in 0.05 to 10 parts by weight.

Preferably, the two-component self etching type bond is a composition comprising a polymerizable monomer (a) having an acidic group, a hydrophilic polymerizable monomer (b), a polymerizable crosslinkable monomers (c), a polymerization initiator (e), a polymerization accelerator (f), and a filler (g).

Regarding the amounts of the respective components to be added in the two-component self etching type bond, it is preferred that the polymerizable monomer (a) having an acidic group be contained in 0 to 80 parts by weight, the polymerizable hydrophilic monomers (b) be contained in 0 to 80 parts by weight and the polymerizable crosslinkable monomers (c) be contained in 1 to 90 parts by weight relative to 100 parts by weight of the whole amount of the polymerizable monomer components, and it is more preferred that the polymerizable monomer (a) having an acidic group be contained in 1 to 70 parts by weight, the polymerizable hydrophilic monomers (b) be contained in 1 to 70 parts by weight and the polymerizable crosslinkable monomers (c) be contained in 5 to 80 parts by weight. Moreover, it is preferred that the polymerization initiator (e) be contained in 0.001 to 30 parts by weight, the polymerization accelerator (f) be contained in 0.001 to 20 parts by weight, and the filler (g) be contained in 0 to 100 parts by weight relative to 100 parts by weight of the whole amount of the polymerizable monomer components, and it is more preferred that the solvent (d) be contained in 5 to 500 parts by weight, the polymerization initiator (e) be contained in 0.05 to 20 parts by weight, the polymerization accelerator (f) be contained in 0.05 to 10 parts by weight, and the filler (g) be contained in 1 to 50 parts by weight. Although the solvent (d) may be used, it is preferred that sufficiently no solvent (d) be contained.

[One-Component Self Etching Type Bond]

A one-component self etching type bond is a bonding material which allows a decalcifying step, a penetration step, and a curing step to be performed together in one stage. The one-component self etching type bond includes a two-agent type characterized in that two agents separated in liquid A and liquid B are mixed just before use and a one-agent type characterized in that one agent is used as it is. Among these, the one-agent type product further simplifies the process and therefore has a greater advantage in use. Preferably, the one-component self etching type bond is a composition comprising a polymerizable monomer (a) having an acidic group, a hydrophilic polymerizable monomer (b), a polymerizable crosslinkable monomers (c), a solvent (d), a polymerization initiator (e), a polymerization accelerator (f), and a filler (g).

Regarding the amounts of the respective components to be added in the one-component self etching type bond, it is preferred that the polymerizable monomer (a) having an acidic group be contained in 1 to 90 parts by weight, the polymerizable hydrophilic monomers (b) be contained in 0 to 90 parts by weight and the polymerizable crosslinkable monomers (c) be contained in 1 to 90 parts by weight relative to 100 parts by weight of the whole amount of the polymerizable monomer components, and it is more preferred that the polymerizable monomer (a) having an acidic group be contained in 5 to 80 parts by weight, the polymerizable hydrophilic monomers (b) be contained in 1 to 80 parts by weight and the polymerizable crosslinkable monomers (c) be contained in 5 to 80 parts by weight. Moreover, it is preferred that the solvent (d) be contained in 1 to 1000 parts by weight, the polymerization initiator (e) be contained in 0.001 to 30 parts by weight, the polymerization accelerator (f) be contained in 0.001 to 20 parts by weight, and the filler (g) be contained in 0 to 100 parts by weight relative to 100 parts by weight of the whole amount of the polymerizable monomer components, and it is more preferred that the solvent (d) be contained in 5 to 500 parts by weight, the polymerization initiator (e) be contained in 0.05 to 20 parts by weight, the polymerization accelerator (f) be contained in 0.05 to 10 parts by weight, and the filler (g) be contained in 1 to 50 parts by weight.

[Adhesive Composite Resin]

In the present invention, it is a preferred embodiment to use a curable composition as an adhesive composite resin. In particular, composite resins in which adhesiveness has been imparted to composite resins for filling have recently been developed. Such resins offer a process more simplified than that of the above-described one-component one-step bonding system and therefore have a greater advantage in use. In using the curable composition as an adhesive composite resin, the curable composition is preferably a composition comprising a polymerizable monomer (a) having an acidic group, a hydrophilic polymerizable monomer (b), a polymerizable crosslinkable monomers (c), a polymerization initiator (e), a polymerization accelerator (f), and a filler (g).

Regarding the amounts of the respective components to be added in the adhesive composite resin, it is preferred that the polymerizable monomer (a) having an acidic group be contained in 1 to 90 parts by weight, the polymerizable hydrophilic monomers (b) be contained in 0 to 90 parts by weight and the polymerizable crosslinkable monomers (c) be contained in 1 to 90 parts by weight relative to 100 parts by weight of the whole amount of the polymerizable monomer components, and it is more preferred that the polymerizable monomer (a) having an acidic group be contained in 5 to 80 parts by weight, the polymerizable hydrophilic monomers (b) be contained in 1 to 80 parts by weight and the polymerizable crosslinkable monomers (c) be contained in 5 to 80 parts by weight. Moreover, it is preferred that the polymerization initiator (e) be contained in 0.001 to 30 parts by weight, the polymerization accelerator (f) be contained in 0.001 to 20 parts by weight, and the filler (g) be contained in 50 to 2000 parts by weight relative to 100 parts by weight of the whole amount of the polymerizable monomer components, and it is more preferred that the polymerization initiator (e) be contained in 0.05 to 20 parts by weight, the polymerization accelerator (f) be contained in 0.05 to 10 parts by weight, and the filler (g) be contained in 100 to 1500 parts by weight.

[Dental Cement]

Furthermore, the use of a curable composition as a dental cement is also a preferred embodiment. Examples of preferable dental cements include a resin cement, a glass ionomer cement, and a resin-reinforced glass ionomer cement. For such a dental cement, a self etching primer or the like may be used as a pretreating agent.

Regarding the amounts of the respective components to be added in the dental cement, it is preferred that the polymerizable monomer (a) having an acidic group be contained in 0 to 90 parts by weight, the polymerizable hydrophilic monomers (b) be contained in 0 to 90 parts by weight and the polymerizable crosslinkable monomers (c) be contained in 1 to 90 parts by weight relative to 100 parts by weight of the whole amount of the polymerizable monomer components, and it is more preferred that the polymerizable monomer (a) having an acidic group be contained in 5 to 80 parts by weight, the polymerizable hydrophilic monomers (b) be contained in 1 to 80 parts by weight and the polymerizable crosslinkable monomers (c) be contained in 5 to 80 parts by weight. Moreover, it is preferred that the polymerization initiator (e) be contained in 0.001 to 30 parts by weight, the polymerization accelerator (f) be contained in 0.001 to 20 parts by weight, and the filler (g) be contained in 50 to 2000 parts by weight relative to 100 parts by weight of the whole amount of the polymerizable monomer components, and it is more preferred that the polymerization initiator (e) be contained in 0.05 to 20 parts by weight, the polymerization accelerator (f) be contained in 0.05 to 10 parts by weight, and the filler (g) be contained in 100 to 1500 parts by weight.

In the present invention, since dentinal tubules will be sealed with dentinal tubules sealant before applying a curable composition to a dentin surface, it becomes possible to suppress pains, hyperesthesia, and so on, and since solid components having adhered to a dentin surface can be removed by scrubbing using water, the adhesive property of a curable composition to a dentin surface becomes good. Accordingly, it is possible to provide a dental treatment method characterized in that dentinal tubules sealant is applied to a dentin surface and then the dentin surface is scrubbed using water. Preferably, it is possible to provide a dental treatment method using dentinal tubules sealant that is to be applied to a dentin surface to fill solid particles into dentinal tubules, wherein the dentinal tubules sealant comprises a water-based dispersing agent in which solid particles are dispersed and which has a solid/liquid ratio of from 0.3 to 2.6, and the method comprises applying the dentinal tubules sealant to a dentin surface to fill solid particles into dentinal tubules, and then removing a solid component adhering to the dentin surface by scrubbing using water. Moreover, the present invention can provide a dental treatment method that comprises applying dentinal tubules sealant to a dentin surface, and then scrubbing the dentin surface by using water, and then applying and curing a curable composition. Preferably, it is possible to provide a dental treatment method using dentinal tubules sealant that is to be applied to a dentin surface to fill solid particles into dentinal tubules, wherein the dentinal tubules sealant comprises a water-based dispersing agent in which solid particles are dispersed and which has a solid/liquid ratio of from 0.3 to 2.6, and the method comprises applying the dentinal tubules sealant to a dentin surface to fill solid particles into dentinal tubules, then removing a solid component adhering to the dentin surface by scrubbing using water, and then applying a curable composition to the dentin surface from which the solid component has been removed, followed by curing the curable composition.

Moreover, in the present invention, it is possible to well provide a dental filling restoration method using dentinal tubules sealant that is to be applied to a dentin surface to fill solid particles into dentinal tubules, wherein the dentinal tubules sealant comprises a water-based dispersing agent in which solid particles are dispersed and which has a solid/liquid ratio of from 0.3 to 2.6, and the method comprises applying the dentinal tubules sealant to a dentin surface to fill solid particles into dentinal tubules, then removing a solid component adhering to the dentin surface by scrubbing using water, and then applying a curable composition, such as a bonding material, to the dentin surface from which the solid component has been removed, followed by curing the curable composition, and further filling a curable composition such as a composite resin.

Moreover, in the present invention, it is possible to provide a dental prosthesis restoration method using a prosthesis, such as an inlay and a crown. In dental prosthesis restoration using an inlay, a temporary sealant may be filled before a prosthesis inlay is mounted, and in dental prosthesis restoration using a crown, a temporary crown may be mounted via a temporary adhesive before the prosthesis crown is mounted. Since such treatment is performed usually under anesthesia, patients do not feel pains, but in actually mounting prostheses such as an inlay and a crown, patients may feel sharp pains when a temporary sealant or a temporary adhesive is removed. In the present invention, pains caused by peeling a temporary sealant or a temporary adhesive can be suppressed since dentinal tubules are filled and sealed with solid particles. Accordingly, when using an inlay as a prosthesis, it is possible to provide a dental prosthesis restoration method using dentinal tubules sealant that is to be applied to a dentin surface to fill solid particles into dentinal tubules, wherein the dentinal tubules sealant comprises a water-based dispersing agent in which solid particles are dispersed and which has a solid/liquid ratio of from 0.3 to 2.6, and the method comprises applying the dentinal tubules sealant to a dentin surface to fill solid particles into dentinal tubules, then removing a solid component adhering to the dentin surface by scrubbing using water, filling a temporary sealant into the dentin surface from which the solid component has been removed, after a lapse of several days or several weeks removing the temporary sealant, and then applying a curable composition such as a dental cement and mounting a prosthesis inlay, followed by curing the curable composition. When using a crown as a prosthesis, it is possible to provide a dental prosthesis restoration method using dentinal tubules sealant that is to be applied to a dentin surface to fill solid particles into dentinal tubules, wherein the dentinal tubules sealant comprises a water-based dispersing agent in which solid particles are dispersed and which has a solid/liquid ratio of from 0.3 to 2.6, and the method comprises applying the dentinal tubules sealant to a dentin surface to fill solid particles into dentinal tubules, then removing a solid component adhering to the dentin surface by scrubbing using water, mounting a temporary crown via a temporary adhesive material to the dentin surface from which the solid component has been removed, after a lapse of several days or several weeks removing the temporary adhesive material and the temporary crown, and then applying a curable composition such as a dental cement and mounting a prosthesis crown, followed by curing the curable composition.

By the dental treatment method of the present invention, it becomes possible to suppress pains, hyperesthesia, and so on since, as described above, dentinal tubules are filled and sealed with solid particles by the dentinal tubules sealant of the present invention before a curable composition is applied to a dentin surface. Specifically, the hyperesthesia caused by opening of dentinal tubules can be treated, and from such a point of view, a method for inhibiting dentinal hypersensitivity using a dentinal hypersensitivity inhibitor comprising dentinal tubules sealant is a preferred embodiment of the present invention. Moreover, the present invention can provide a kit of a dental treatment material comprising dentinal tubules sealant and a curable composition in combination. Specifically, it is possible to provide a dental treatment material comprising in combination dentinal tubules sealant that comprises a water-based dispersing agent in which solid particles are dispersed and which has a solid/liquid ratio of from 0.3 to 2.6, the dentinal tubules sealant being capable of, after being applied to a dentin surface to fill dentinal tubules with solid particles, allowing a solid component adhering to the dentin surface to be removed by scrubbing using water, and a curable composition that is to be applied to and then cured on the dentin surface from which the solid component has been removed.

EXAMPLES

The present invention is described in detail with reference to examples and comparative examples, but the invention is not limited to these examples. The materials, the testing methods, and so on which are used in the examples and the comparative examples are summarized below. Regarding an average particle diameter in the examples, measurement was conducted using a laser diffraction type particle size distribution analyzer ("SALD-2100" manufactured by Shimadzu Corporation), and a median diameter calculated from the result of the measurement was defined as the average particle diameter.

[Solid Particles]
TTCP: average particle diameter: 5.0 µm, tetracalcium phosphate [$Ca_4(PO_4)_2O$], TTCP produced by Taihei Chemical Industrial Co., Ltd.
DCPA: average particle diameter: 26.6 µm, anhydrous calcium hydrogen phosphate [$CaHPO_4$], DCPA produced by Taihei Chemical Industrial Co., Ltd.

DCPA: average particle diameter: 43.5 μm, anhydrous calcium hydrogen phosphate [CaHPO$_4$], produced by Taihei Chemical Industrial Co., Ltd.
HAP: average particle diameter: 26.9 μm, hydroxyapatite [Ca$_{10}$(PO$_4$)$_6$(OH)$_2$], HAP-100 produced by Taihei Chemical Industrial Co., Ltd.
Melamine resin: average particle diameter: 0.5 μm, OPTI-BEADS 500S produced by Nissan Chemical Industries, Ltd.
[Applicator]
Cotton ball: COTTON PELLET #3 produced by Richmond
Microbrush: Microbrush Superfine produced by Microbrush Corporation
Sponge: Sponge (NL) produced by Kuraray Medical Inc.
Cotton swab: Neo Swab No. 3 produced by Hakujuji Co., Ltd.
Small brush: Disposable Brush Tip white produced by Kuraray Medical Inc.
[Components of Polymerizable Compositions]
MDP: 10-Methacryloyloxydecyl dihydrogen phosphate
HEMA: 2-Hydroxyethylmethacrylate
MDMA: 3,4-Di-O-methacryloyl-D-mannitol.
BisGMA: 2,2-Bis[(4-(3-methacryloyloxy)-2-hydroxypropoxyphenyl)]propane
TEGDMA: Triethylene glycol dimethacrylate
TMDPO: 2,4,6-Trimethylbenzoyldiphenylphosphine oxide
NPG: Neopentyl glycol dimethacrylate
THP: 1,1,3,3-Tetramethylbutyl hydroperoxide
BHT: 2,6-Di-tert-butyl-4-methylphenol
PTU: 1-(2-Pyridyl)-2-thiourea
Inorganic filler 1: 8972 produced by NIPPON AEROSIL CO., LTD.
Inorganic filler 2: Silane-treated barium glass powder
Inorganic filler 3: Silane-treated colloidal silica powder
[Preparation of Solid Particles]
(1) Preparation of DCPA (Average Particle Diameter: 1.1 μm, 0.7 μm, 5.0 μm)
A slurry was prepared by adding 50 g of DCPA having an average particle diameter of 26.6 μm, 240 g of 95% ethanol ("Ethanol (95)" produced by Wako Pure Chemical Industries, Ltd.) and 480 g of zirconia balls having a diameter of 10 mm into a 1000-ml grinding pot made of alumina ("HD-B-104 Pot Mill" manufactured by Nikkato Corporation) and subsequently subjecting wet vibration pulverization at a rotation speed of 1500 rpm for 15 hours. DCPA having an average particle diameter of 1.1 μm was obtained by evaporating ethanol in the slurry with a rotary evaporator, followed by drying at 60° C. for 6 hours. DCPA having an average particle diameter of 0.7 μm and DCPA having an average particle diameter of 5.0 μm were obtained similarly by the preparation method for the DCPA having an average particle diameter of 1.1 μm except for adjusting the pulverization time to 30 hours and 7 hours, respectively.
(2) Preparation of Ca$_3$SiO$_5$ (Average Particle Diameter: 13.2 μm)
Into a 1-L separable flask were placed 354.0 g of calcium nitrate tetrahydrate and 200 ml of distilled water. Under stirring with a mechanical stirrer, a solution prepared by dissolving 104.0 g of tetraethoxysilane in 120 ml of ethanol was added. A solution prepared by dissolving 5.0 g of nitric acid in 5 ml of water was added and stirred at 60° C. for 24 hours. The resulting gel was transferred to a vat made of stainless steel and then dried at 120° C. for 72 hours. Subsequently, the resultant was transferred to an alumina crucible and calcined at 1450° C. for 3 hours, so that 109.0 g of white solid was obtained. A 20-g portion of the resulting white solid was pulverized with a piston stirrer for 1 hour and thereby desired Ca$_3$SiO$_5$ was prepared.

[Preparation of Inorganic Filler]
(1) Inorganic Filler 2
Barium glass (manufactured by STEC Inc., Product Code: "Raysorb E-3000") was crushed with a ball mill and thus barium glass powder was obtained. The mean particle diameter of the barium glass powder thus obtained was measured with a laser diffraction particle size distribution analyzer (manufactured by Shimadzu Corporation, Type "SALD-2100") and it was 2.4 μm. The surface treatment was performed by a conventional method using 3 parts by weight of 3-methacryloyloxypropyltrimethoxysilane with respect to 100 parts by weight of the barium glass powder. Thus, silane-treated barium glass powder was obtained.
(2) Inorganic Filler 3
To 100 parts by weight of distilled water were added 0.3 parts by weight of acetic acid and 3 parts by weight of 3-methacryloyloxypropyltrimethoxysilane, which was then stirred. Further 50 parts by weight of colloidal silica powder (manufactured by NIPPON AEROSIL CO., LTD., Product Code: "Aerosil OX50") was added thereto, which was then stirred for one hour. After water was removed by freeze drying, this was heat-treated at 80° C. for five hours and thus silane-treated colloidal silica powder was obtained.
[Preparation of Curable Composition]
(1) One-Component Self Etching Type Bond
A one-component self etching type bond was prepared by mixing the following components at normal temperature.
One-component self etching type bond composition:

| | |
|---|---|
| MDP | 10 parts by weight |
| BisGMA | 30 parts by weight |
| HEMA | 30 parts by weight |
| TMDPO | 3 parts by weight |
| Water | 15 parts by weight |
| Ethanol | 15 parts by weight |
| Inorganic filler 1 | 5 parts by weight |

(2) Two-Component Self Etching Type Bond
A primer and a bond were prepared by mixing the following components at normal temperature.
Primer Composition:

| | |
|---|---|
| MDP | 20 parts by weight |
| TEGDMA | 35 parts by weight |
| HEMA | 45 parts by weight |
| TMDPO | 3 parts by weight |
| Water | 50 parts by weight |
| Ethanol | 50 parts by weight |

Bond Composition:

| | |
|---|---|
| BisGMA | 40 parts by weight |
| HEMA | 40 parts by weight |
| NPG | 20 parts by weight |
| TMDPO | 3 parts by weight |
| Inorganic filler 1 | 7 parts by weight |

(3) One-component Total Etching Type Bond
A one-component total etching type bond was prepared by mixing the following components at normal temperature.
Total Etching Type Bond Composition:

| | |
|---|---|
| MDP | 20 parts by weight |
| BisGMA | 25 parts by weight |
| HEMA | 15 parts by weight |

-continued

| | |
|---|---|
| TEGDMA | 10 parts by weight |
| TMDPO | 3 parts by weight |
| Ethanol | 30 parts by weight |
| Inorganic filler 1 | 5 parts by weight |

(4) Cement

A cement was prepared by mixing the following components at normal temperature. Agent A and agent 8 were prepared in two portions and were used by being mixed in equivolume just before use.

Cement Composition Agent A:

| | |
|---|---|
| MDP | 30 parts by weight |
| MDMA | 20 parts by weight |
| HEMA | 50 parts by weight |
| THP | 3 parts by weight |
| BHT | 30 parts by weight |
| Inorganic filler 2 | 140 parts by weight |
| Inorganic filler 3 | 45 parts by weight |

Cement Composition Agent B:

| | |
|---|---|
| HEMA | 50 parts by weight |
| TEGDMA | 50 parts by weight |
| PTU | 1 part by weight |
| BHT | 0.05 parts by weight |
| Inorganic filler 2 | 140 parts by weight |
| Inorganic filler 3 | 45 parts by weight |

[Evaluation of Dentinal Tubules Sealant]

(1) Preparation of Dentinal Tubules Sealant

Dentinal tubules sealants 1 through 14 were prepared by mixing materials in the compounding ratios shown in Table 1.

(2) Spreadability

Dentinal tubules sealant 1 obtained above was applied with a microbrush to a slide glass within a range of 14 mm×14 mm and then the slide glass was erected vertically. The applied surface was observed visually and when neither an agglomerate of a solid component nor a drip was observed, spreadability was judged to be good. Spreadability was evaluated similarly for dentinal tubules sealants 2 through 14. Cases where spreadability was good were represented by "A" and cases where spreadability was not good were represented by "B." The results thus obtained are indicated together in Table 1.

(3) Dentinal Tubules Sealability

The tooth root of an anterior tooth of a bovine mandibular was cut away and then the pulp was removed. The labial surface was ground with #80 silicon carbide paper (manufactured by Nihon Kenshi Co., Ltd.) under running water, and thereby a flat surface of dentin was exposed. Moreover, the lingual surface was ground with #80 silicon carbide paper under running water, and thereby a 3-mm thick sample was obtained. The sample thus obtained was ground with #1000 silicon carbide paper (manufactured by Nihon Kenshi Co., Ltd.) under running water and subsequently was ground using wrapping film (manufactured by Sumitomo 3M Ltd.) with #1200, #3000, and #8000 in the order. A 3% by weight EDTA solution was applied to the dentin surface, which was then washed with running water 30 seconds later. Subsequently, a 10% by weight sodium hypochlorite solution was applied and then it was washed with running water 2 minutes later. The dentinal tubules sealant 1 obtained above was rubbed into a 4 mm×4 mm area of the dentin surface for 30 seconds with a microbrush. Subsequently, scrubbing was performed with a cotton ball for 30 seconds under running water. For the sample obtained, the dentinal tubules sealant-treated surface after drying and metal vapor deposition treatment was observed at a magnification of 3000 by using a scanning electron microscope (S-3500N, manufactured by Hitachi High-Technologies Corporation). The proportion of the sealed dentinal tubules to all dentinal tubules was calculated and it was considered as dentinal tubules sealing ratio. Dentinal tubules sealability was evaluated similarly for dentinal tubules sealants 2 through 14. The results thus obtained are indicated together in Table 1.

An emulsion was obtained in accordance with Example 1 of Patent Document 1. The resulting emulsion was diluted with distilled water so that the solid concentration might become 5 wt %, thereby preparing sealant 15. In dentinal tubules sealability test, a bovine mandibular incisor was subjected to a treatment including applying a 10% by weight sodium hypochlorite solution and washing with running water 2 minutes later. Sealant 15 was applied to a 4 mm×4 mm area of the dentin surface and was allowed to stand for 1 minute. Then, the applied sealant 15 was dried by air-blowing the surface, so that a film was formed. Subsequently, scrubbing was performed with a cotton ball for 30 seconds under running water. For the sample obtained, the dentinal tubules sealant-treated surface after drying and metal vapor deposition treatment was observed at a magnification of 3000 by using a scanning electron microscope (S-3500N, manufactured by Hitachi High-Technologies Corporation). The proportion of the sealed dentinal tubules to all dentinal tubules was calculated and it was considered as dentinal tubules sealing ratio. The dentinal tubules sealing ratio in the case where sealant 15 was used was 22%.

In accordance with Example 1 of Patent Document 2, liquid A resulting from the adjustment of the pH of a 5% aqueous disodium hydrogen phosphate solution to 7.4 with a 5% aqueous sodium dihydrogen phosphate solution and liquid B resulting from the adjustment of the pH of a 10% aqueous calcium chloride solution to 7.4 with a 5% aqueous hydrochloric acid solution were prepared, and thereby sealant 16 was obtained. In dentinal tubules sealability test, a bovine mandibular incisor was subjected to a treatment including applying a 10% by weight sodium hypochlorite solution and washing with running water 2 minutes later. Sealant 16 was applied to a 4 mm×4 mm area of a dentin surface within the circular hole in the order, liquid A and then liquid B, and after being allowed to stand for 1 minute, it was dried by air-blowing. Subsequently, scrubbing was performed with a cotton ball for 30 seconds under running water. For the sample obtained, the dentinal tubules sealant-treated surface after drying and metal vapor deposition treatment was observed at a magnification of 3000 by using a scanning electron microscope (S-3500N, manufactured by Hitachi High-Technologies Corporation). The proportion of the sealed dentinal tubules to all dentinal tubules was calculated and it was considered as dentinal tubules sealing ratio. The dentinal tubules sealing ratio in the case where sealant 16 was used was 25%.

In accordance with Example 1 of Patent Document 3, a dispersion liquid of fluoroaluminosilicate glass fine particles and an aqueous phosphoric acid solution were prepared, and thereby sealant 17 was obtained. In dentinal tubules sealability test, a bovine mandibular incisor was subjected to a treatment including applying a 10% by weight sodium hypochlorite solution and washing with running water 2 minutes later. After mixing sealant 17 in equivolume, it was rubbed to a 4 mm×4 mm area of a dentin surface and rubbed for 20 seconds. After washing with running water, it was dried by air-blowing. Subsequently, scrubbing was performed with a cotton ball for 30 seconds under running water. For the sample obtained, the dentinal tubules sealant-treated surface after drying and metal vapor deposition treatment was observed at a magnification of 3000 by using a scanning electron microscope (S-3500N, manufactured by Hitachi High-Technologies Corporation). The proportion of the sealed dentinal tubules to all dentinal tubules was calculated and it was considered as dentinal tubules sealing ratio. The dentinal tubules sealing ratio in the case where sealant 17 was used was 13%.

To the surface of the resulting cured composite resin for dental filling, one end face (circular section) of a cylindrical rod (7 mm in diameter and 2.5 cm in length) made of stainless steel was adhered with a commercially available dental resin cement (trade name "PANAVIA 21" produced by Kuraray Medical Inc.). After bonding, this sample was allowed to stand still at room temperature for 30 minutes and was then immersed in distilled water. The resultant sample that had been immersed in distilled water was allowed to standstill for

TABLE 1

| | | Seal-ant 1 | Seal-ant 2 | Seal-ant 3 | Seal-ant 4 | Seal-ant 5 | Seal-ant 6 | Seal-ant 7 | Seal-ant 8 | Seal-ant 9 | Seal-ant 10 | Seal-ant 11 | Seal-ant 12 | Seal-ant 13 | Seal-ant 14 |
|---|---|---|---|---|---|---|---|---|---|---|---|---|---|---|---|
| TTCP (5.0 μm) | (part by weight) | 39.7 | 24.3 | 45.9 | 52.1 | 54.5 | | | | | | | | | |
| DCPA (0.7 μm) | (part by weight) | | | | | | 50.0 | | | | | | | 16.7 | 75.0 |
| DCPA (1.1 μm) | (part by weight) | 14.8 | 9.0 | 17.1 | 19.3 | | | | | | | | | | |
| DCPA (5.0 μm) | (part by weight) | | | | | | | 50.0 | | | | | | | |
| DCPA (43.5 μm) | (part by weight) | | | | | | | | 50.0 | | | | | | |
| HAP (26.9 μm) | (part by weight) | | | | | | | | | 44.4 | 28.6 | | | | |
| Ca$_3$SiO$_5$ (13.2 μm) | (part by weight) | | | | | | | | | | | 54.5 | | | |
| Melamine resin (0.5 μm) | (part by weight) | | | | | | | | | | | | 50.0 | | |
| Purified water | (part by weight) | 45.5 | 66.7 | 37.0 | 28.6 | 45.5 | 50.0 | 50.0 | 50.0 | 55.6 | 71.4 | 45.5 | 50.0 | 83.3 | 25.0 |
| Total | (part by weight) | 100 | 100 | 100 | 100 | 100 | 100 | 100 | 100 | 100 | 100 | 100 | 100 | 100 | 100 |
| Solid/liquid ratio | | 1.2 | 0.5 | 1.7 | 2.5 | 1.2 | 1.0 | 1.0 | 1.0 | 0.8 | 0.4 | 1.2 | 1.0 | 0.2 | 3.0 |
| Spreadability | | A | A | A | A | A | A | A | A | A | A | A | A | B | B |
| Dentinal tubules sealing ratio (%) | | 100 | 91 | 99 | 90 | 95 | 94 | 93 | 52 | 71 | 62 | 82 | 90 | — | — |

[Evaluation of Adhesive Property]
(1) One-Component Self Etching Type Bond

The labial surface of a bovine mandibular incisor was ground with #80 silicon carbide paper (manufactured by Nihon Kenshi Co., Ltd.) under running water, and thereby a flat surface of dentin was exposed. Subsequently, the sample was further ground with #1000 silicon carbide paper (manufactured by Nihon Kenshi Co., Ltd.) under running water. After completion of the grinding, water on the surface was removed by air blowing and thereby an adherent sample was obtained.

To an area of 4 mm×4 mm of the dentin surface of the resulting adherent sample, dentinal tubules sealant was rubbed for 30 second with a microbrush. Subsequently, a dentin surface was cleaned by a specified cleaning method using a specified applicator.

An adhesive tape with a thickness of about 150 μm having a circular hole whose diameter was 3 mm was attached to the sealant-treated surface of the adherent sample and thereby the adhesive area was defined. A one-component bonding material composition was applied within the round hole with a brush, followed by being allowed to stand for 20 seconds. Then, the surface was dried by air-blowing until the one-component bonding material composition applied lost its flowability. Then, the resultant was irradiated with light for 20 seconds using a dental visible light irradiator "JET LIGHT 3000" (manufactured by J. Morita USA, Inc.), thereby curing the one-component bonding material composition applied.

A dental filling composite resin (manufactured by Kuraray Medical Inc., "CLEARFIL AP-X" (trade name, registered trademark)) was applied to the surface of the resultant cured product of the one-component bonding material composition, and it was then covered with a mold release film (polyester). Next, slide glass was placed on the mold release film to press it, and thereby the surface of the applied composite resin was smoothed. Subsequently, the composite resin was irradiated with light for 20 seconds using the aforementioned unit "JET LITE 3000" through the mold release film. Thus, the composite resin was cured.

24 hours inside a thermostat whose temperature was maintained at 37° C. Thus, a bonding test sample was produced.

The tensile adhesion strengths of five bonding test samples were measured with a universal testing machine (manufactured by Shimadzu Corporation), with the crosshead speed being set at 2 mm/min, and the average value thereof was taken as tensile adhesion strength. A rupture surfaces after the test were observed and the number of samples in which the dentin side was broken was considered as the number of adherent breaks.

The tensile adhesion strength and the number of adherent breaks were determined in the same manner as those described above except for failing to use dentinal tubules sealant in the above-described measurement of tensile adhesion strength. As a result, the tensile adhesion strength was 17.7 MPa and the number of adherent breaks was 4.

(2) Two-Component Self Etching Type Bond

The adhesive property was evaluated by the same method as (1) except for using a two-component self etching type bond instead of the one-component self etching type bond. Specifically, the primer composition prepared above was applied into a circular hole using a brush and was then allowed to stand for 20 seconds. Thereafter, the surface was air-blown and thereby the excess of the primer was removed. Subsequently, a bonding material composition was applied and then air was blown lightly so that the thickness of the coating film might become uniform. Then, the resultant was irradiated with light for 20 seconds using a dental visible light irradiator "JET LIGHT 3000" (manufactured by J. Morita USA, Inc.), thereby curing the bonding material composition applied.

The tensile adhesion strength and the number of adherent breaks were determined in the same manner as those described in (1) above except for failing to use dentinal tubules sealant and using the two-component self etching type bond of the above-described (2) instead of the one-component self etching type bond in the measurement of tensile adhesion strength of the above-described (1). As a result, the tensile adhesion strength was 18.4 MPa and the number of adherent breaks was 5.

(3) One-Component Total Etching Type Bond

The adhesive property was evaluated by the same method as (1) except for performing phosphoric acid treatment before defining an adhesive area by attaching an adhesive tape and using a one-component total etching type bond instead of the one-component self etching type bond. A sealant was used before or after phosphoric acid etching. K-ETCHANT GEL (produced by KURARAY MEDICAL INC.) was used as a phosphoric acid etching material. K-ETCHANT GEL was applied with a small brush, allowed to stand for 15 seconds, and then washed with running water. The one-component total etching type bond was applied into a circular hole of 3 mm in diameter formed in an adhesive tape having a defined adhesive area. Thereafter, the surface thereof was air-blown and thereby the composition was dried until it lost flowability. Then, the resultant was irradiated with light for 20 seconds using a dental visible light irradiator "JET LIGHT 3000" (manufactured by J. Morita USA, Inc.), thereby curing the one-component total etching type bonding material composition applied.

The tensile adhesion strength and the number of adherent breaks were determined in the same manner as those described in (1) above except for failing to use dentinal tubules sealant and using the one-component total etching type bond of the above-described (3) instead of the one-component self etching type bond in the measurement of tensile adhesion strength of the above-described (1). As a result, the tensile adhesion strength was 16.9 MPa and the number of adherent breaks was 2.

(4) Cement

The adhesive property was evaluated by the same method as (1) except for using a cement instead of the one-component self etching bond. Specifically, a paste prepared by mixing the cement composition A and the cement composition B prepared as described above was applied in a mound form onto one end face (circular section) of a stainless-steel cylindrical rod (with a diameter of 7 mm and a length of 2.5 cm). The end face on which the mound of cement composition was made was placed on the circular hole to press it so that the center of the stainless-steel cylindrical rod coincided with the center of the circular hole. Thus, the stainless-steel cylindrical rod was set vertically to the tooth surface. After setting the stainless-steel cylindrical rod, excess cement composition flowing out around the rod was removed with an instrument, and this sample was allowed to stand still at room temperature for 30 minutes and was then immersed in distilled water. The resultant sample that had been immersed in distilled water was allowed to stand still for 24 hours inside a thermostat whose temperature was maintained at 37° C. Thus, a bonding test sample was produced.

The tensile adhesion strength and the number of adherent breaks were determined in the same manner as those described in (1) above except for failing to use dentinal tubules sealant and using the cement (4) described above instead of the one-component self etching type bond in the measurement of tensile adhesion strength of the above-described (1). As a result, the tensile adhesion strength was 9.8 MPa and the number of adherent breaks was 0.

Examples 1 to 14

Using the dentinal tubules sealants and the curable composition shown in Table 2, adhesive property was evaluated in accordance with the methods (1) through (4) described above in the evaluation of adhesive property depending upon the type of the curable composition used. In the evaluation of adhesive property, after the treatment of a dentin surface using dentinal tubules sealant, the dentin surface was cleaned by scrubbing by using the applicator shown in Table 2. In Example 8, dentinal tubules sealant was used after phosphoric acid etching. In Example 9, dentinal tubules sealant was used before phosphoric acid etching. The evaluation results obtained are summarized in Table 2.

Example 15

Using the dentinal tubules sealant and the cement composition shown in Table 3, adhesive property was evaluated in accordance with the method (4) described above in the evaluation of adhesive property. In the evaluation of adhesive property, after the treatment of a dentin surface using dentinal tubules sealant, the dentin surface was cleaned by scrubbing by using a cotton ball. The evaluation results obtained are summarized in Table 3.

Comparative Examples 1 to 7

Using the dentinal tubules sealants and the curable composition shown in Table 2, adhesive property was evaluated in accordance with the methods (1) and (2) described above in the evaluation of adhesive property depending upon the type of the curable composition used. In the evaluation of adhesive property, after the treatment of a dentin surface using dentinal tubules sealant, the dentin surface was cleaned by scrubbing by using the applicator shown in Table 2.

Comparative Example 8

An emulsion was obtained in accordance with Example 1 of Patent Document 1. The resulting emulsion was diluted with distilled water so that the solid concentration might become 5 wt %, thereby preparing sealant 15. An adhesive tape with a thickness of about 150 μm having a circular hole whose diameter was 3 mm was attached to the dentin surface of an adherent sample obtained in the same manner as in the above-described (1) in the adhesive property evaluation and thereby the adhesive area was defined. The above-described testing sample was applied into the above-mentioned circular hole and was then allowed to stand for 1 minute. Thereafter, the surface thereof was air-blown and thereby the applied testing sample was dried, so that a film was formed. A one-component bonding material composition was applied onto the formed film with a brush, followed by being allowed to stand for 20 seconds. Then, the surface was dried by air-blowing until the one-component bonding material composition applied lost its flowability. Then, the resultant was irradiated with light for 20 seconds using a dental visible light irradiator "JET LIGHT 3000" (manufactured by J. Morita USA, Inc.), thereby curing the one-component bonding material composition applied. Henceforth, the adhesive property was evaluated in the same manner as the above-described (1) in the adhesive property evaluation.

Comparative Example 9

In accordance with Example 1 of Patent Document 2, liquid A resulting from the adjustment of the pH of a 5% aqueous disodium hydrogen phosphate solution to 7.4 with a 5% aqueous sodium dihydrogen phosphate solution and liquid B resulting from the adjustment of the pH of a 10% aqueous calcium chloride solution to 7.4 with a 5% aqueous hydrochloric acid solution were prepared, and thereby sealant 16 was obtained. An adhesive tape with a thickness of about 150 µm having a circular hole whose diameter was 3 mm was attached to the dentin surface of an adherent sample obtained in the same manner as in the above-described (1) in the adhesive property evaluation and thereby the adhesive area was defined. The above-mentioned testing sample was applied to within the circular hole in the order, liquid A and then liquid B, and after being allowed to stand for 1 minute, it was dried by air-blowing. A one-component bonding material composition was applied within the round hole with a brush, followed by being allowed to stand for 20 seconds. Then, the surface was dried by air-blowing until the one-component bonding material composition applied lost its flowability. Then, the resultant was irradiated with light for 20 seconds using a dental visible light irradiator "JET LIGHT 3000" (manufactured by J. Morita USA, Inc.), thereby curing the one-component bonding material composition applied. Henceforth, the adhesive property was evaluated in the same manner as the above-described (1) in the adhesive property evaluation.

Comparative Example 10

In accordance with Example 1 of Patent Document 3, a dispersion liquid of fluoroaluminasilicate glass fine particles and an aqueous phosphoric acid solution were prepared, and thereby sealant 17 was obtained. An adhesive tape with a thickness of about 150 µm having a circular hole whose diameter was 3 mm was attached to the dentin surface of an adherent sample obtained in the same manner as in the above-described (1) in the adhesive property evaluation and thereby the adhesive area was defined. After the above-mentioned testing sample was mixed in equivolume, it was applied to within the circular hole and then rubbed for 20 seconds. After washing with running water, it was dried by air-blowing. A one-component bonding material composition was applied within the round hole with a brush, followed by being allowed to stand for 20 seconds. Then, the surface was dried by air-blowing until the one-component bonding material composition applied lost its flowability. Then, the resultant was irradiated with light for 20 seconds using a dental visible light irradiator "JET LIGHT 3000" (manufactured by J. Morita USA, Inc.), thereby curing the one-component bonding material composition applied. Henceforth, the adhesive property was evaluated in the same manner as the above-described (1) in the adhesive property evaluation.

Comparative Example 11

Adhesive property was evaluated in accordance with the method (4) described above in the evaluation of adhesive property in the same manner as in Example 15 except for cleaning a dentin surface with running water instead of scrubbing a dentin surface using a cotton ball after treating the dentin surface using dentinal tubules sealant in Example 15. The evaluation results obtained are summarized in Table 3.

TABLE 2

| | Dentinal tubules sealant | Curable composition | Applicator | Cleaning method | Adhesion strength (MPa) | Number of adherent breaks |
|---|---|---|---|---|---|---|
| Example 1 | Sealant 1 | 1-Component SE | Cotton ball | Scrubbing | 18.8 | 4 |
| Example 2 | Sealant 5 | 1-Component SE | Cotton ball | Scrubbing | 17.7 | 4 |
| Example 3 | Sealant 6 | 1-Component SE | Cotton ball | Scrubbing | 18.0 | 3 |
| Example 4 | Sealant 7 | 1-Component SE | Cotton ball | Scrubbing | 17.4 | 3 |
| Example 5 | Sealant 9 | 1-Component SE | Cotton ball | Scrubbing | 18.1 | 3 |
| Example 6 | Sealant 11 | 1-Component SE | Cotton ball | Scrubbing | 17.8 | 4 |
| Example 7 | Sealant 12 | 1-Component SE | Cotton ball | Scrubbing | 17.9 | 3 |
| Example 8 | Sealant 1 | 1-Component TE | Cotton ball | Scrubbing | 16.0 | 2 |
| Example 9 | Sealant 1 | 1-Component TE | Cotton ball | Scrubbing | 17.1 | 3 |
| Example 10 | Sealant 1 | 2-Component SE | Cotton ball | Scrubbing | 18.0 | 5 |
| Example 11 | Sealant 1 | 1-Component SE | Microbrush | Scrubbing | 17.9 | 4 |
| Example 12 | Sealant 1 | 1-Component SE | Sponge | Scrubbing | 17.5 | 3 |
| Example 13 | Sealant 1 | 1-Component SE | Cotton swab | Scrubbing | 18.2 | 4 |
| Example 14 | Sealant 1 | 1-Component SE | Small brush | Scrubbing | 17.6 | 3 |
| Comparative Example 1 | Sealant 1 | 1-Component SE | Cotton ball | Wiping | 11.2 | 0 |
| Comparative Example 2 | Sealant 1 | 1-Component SE | — | Running water | 7.2 | 0 |
| Comparative Example 3 | Sealant 7 | 1-Component SE | — | Running water | 7.5 | 0 |
| Comparative Example 4 | Sealant 9 | 1-Component SE | — | Running water | 8.2 | 0 |
| Comparative Example 5 | Sealant 11 | 1-Component SE | — | Running water | 8.9 | 0 |
| Comparative Example 6 | Sealant 12 | 1-Component SE | — | Running water | 9.3 | 0 |
| Comparative Example 7 | Sealant 1 | 2-Component SE | — | Running water | 16.1 | 1 |
| Comparative Example 8 | Sealant 15 | 1-Component SE | — | — | 4.0 | 0 |
| Comparative Example 9 | Sealant 16 | 1-Component SE | — | — | 5.0 | 0 |
| Comparative Example 10 | Sealant 17 | 1-Component SE | — | — | 5.3 | 0 |

TABLE 3

| | Dentinal tubules sealant | Curable composition | Applicator | Cleaning method | Adhesion strength (MPa) | Number of adherent breaks |
|---|---|---|---|---|---|---|
| Example 15 | Sealant 1 | Cement | Cotton ball | Scrubbing | 10.0 | 0 |
| Comparative Example 11 | Sealant 1 | Cement | — | Running water | 4.0 | 0 |

[Evaluation of Pain in Prosthetic Restoration Treatment]

Of 30 patients needing prosthetic restoration treatment after performing the formation of a deep cavity extending to near the pulp, 15 patients were taken as a group of using sealant 1 and remaining 15 patients were taken as a group of failing to use sealant 1. In the group of using sealant 1, sealant 1 was rubbed for 30 seconds to a cavity (prepared dentin for restoration) to prosthetically restoration and excess sealant 1 was removed by water washing, and then the cavity was cleaned by wiping for 10 seconds with a cotton ball wet with water. After taking an impression of the cavity, the cavity was sealed with a temporary sealant (HY-Bond Temporary Cement Soft, produced by SHOFU, INC.), and the patients went home. Conversely, in the group of not using sealant 1, for a cavity (prepared dentin for restoration) to prosthetically restoration, after the impression of the cavity was taken, the cavity was sealed with the temporary sealant described above and then the patient went home. For the patients returned one week later, the temporary sealant was removed with a scaler from the cavity. At this time, the patient feels a pain especially when the temporary sealant adhering to a tooth is ground with a scaler because generally, anesthesia is not applied. Regarding this pain, the pains felt by the patients of the group of using sealant 1 and the patients of the group of not using sealant 1 were recorded according to the scores given below. In the group of using sealant 1, there were eight patients with score 0, seven patients with score 1, and zero patients with score 2, whereas in the group of not using sealant 1, there were zero patients with score 0, two patients of score 1, and thirteen patients with score 2.

Score of Pain
0: No pain is felt.
1: A slight pain is felt.
2: A severe pain is felt.

The invention claimed is:

1. A dental treatment method, comprising:
applying a dentinal tubules sealant comprising a water-based dispersing agent in which solid particles are dispersed and which has a solid/liquid weight ratio of from 0.3 to 2.6, to a dentin surface to fill the solid particles into dentinal tubules;
removing remaining solid particles of the dentinal tubules sealant adhering to the dentin surface and not filled into the dentinal tubules by scrubbing with water; and then, applying a curable composition to the dentin surface with the filled dentinal tubules and from which the remaining solid particles of the dentinal tubules sealant adhering to the dentin surface have been removed, followed by curing the curable composition.

2. A method for inhibiting dentinal hypersensitivity, the method comprising:
applying a dentinal hypersensitivity inhibitor comprising a dentinal tubules sealant comprising a water-based dispersing agent in which solid particles are dispersed and which has a solid/liquid weight ratio of from 0.3 to 2.6, to a dentin surface to fill the solid particles into dentinal tubules;
removing remaining solid particles of the dentin tubules sealant adhering to the dentin surface and not filled into the dentinal tubules by scrubbing with water; and then, applying a curable composition to the dentin surface with the filled dentinal tubules and from which the remaining solid particles of the dentinal tubules sealant adhering to the dentin surface have been removed, followed by curing the curable composition.

3. The dental treatment method of claim 1, wherein the solid particles are at least one calcium phosphate selected from the group consisting of tetracalcium phosphate [$Ca_4(PO_4)_2O$], anhydrous calcium hydrogen phosphate [$CaHPO_4$], and calcium hydrogen phosphate dihydrate [$CaHPO_4 \cdot 2H_2O$].

4. The dental treatment method of claim 1, wherein an average particle diameter of the solid particles is from 0.05 to 40 µm.

5. The method for inhibiting dentinal hypersensitivity of claim 2, wherein the solid particles are at least one calcium phosphate selected from the group consisting of tetracalcium phosphate [$Ca_4(PO_4)_2O$], anhydrous calcium hydrogen phosphate [$CaHPO_4$], and calcium hydrogen phosphate dihydrate [$CaHPO_4 \cdot 2H_2O$].

6. The method for inhibiting dentinal hypersensitivity of claim 2, wherein an average particle diameter of the solid particles is from 0.05 to 40 µm.

* * * * *